United States Patent [19]
Ecker et al.

[11] Patent Number: 5,899,927
[45] Date of Patent: May 4, 1999

[54] DETECTION OF PRESSURE WAVES TRANSMITTED THROUGH CATHETER/LEAD BODY

[75] Inventors: Robert M. Ecker, Anoka; Lawrence C. McClure, Maple Grove; John D. Wahlstrand, Shoreview, all of Minn.

[73] Assignee: Medtronic, Inc., Minneapolis, Minn.

[21] Appl. No.: 08/953,092

[22] Filed: Oct. 17, 1997

Related U.S. Application Data

[63] Continuation of application No. 08/625,029, Mar. 28, 1996, abandoned.

[51] Int. Cl.$^6$ ........................................... A61B 5/00
[52] U.S. Cl. ............................................. 607/23; 600/486
[58] Field of Search .................................. 600/486, 480, 600/541; 607/17, 23, 24

[56] References Cited

U.S. PATENT DOCUMENTS

| | | |
|---|---|---|
| Re. 32,652 | 4/1988 | Nakamura . |
| 3,555,187 | 1/1971 | Rowley . |
| 3,815,611 | 6/1974 | Denniston . |
| 4,023,562 | 5/1977 | Hynecek . |
| 4,114,628 | 9/1978 | Rizk . |
| 4,407,296 | 10/1983 | Anderson . |
| 4,432,372 | 2/1984 | Monroe . |
| 4,485,813 | 12/1984 | Anderson . |
| 4,763,646 | 8/1988 | Lekholm . |
| 4,846,191 | 7/1989 | Brockway et al. ............... 128/748 |
| 4,858,615 | 8/1989 | Meinema . |
| 4,967,755 | 11/1990 | Pohndorf . |
| 4,998,977 | 3/1991 | Preiss et al. ...................... 128/673 |
| 5,063,927 | 11/1991 | Webb . |
| 5,069,680 | 12/1991 | Grandjean . |
| 5,070,605 | 12/1991 | Daglow . |

(List continued on next page.)

FOREIGN PATENT DOCUMENTS

| | | |
|---|---|---|
| 0089014 | 9/1983 | European Pat. Off. . |
| 0151689 | 8/1985 | European Pat. Off. . |
| 9413200 | 6/1994 | WIPO . |
| 9522878 | 8/1995 | WIPO . |

OTHER PUBLICATIONS

Published Anonymously, Research Disclosure "Use of Heart Valve Sounds as Input to Cardiac Assist Devices", No. 37150.

*Primary Examiner*—Robert L. Nasser
*Attorney, Agent, or Firm*—Michael B. Atlass; Harold R. Patton

[57] ABSTRACT

In an implanted medical device, a method and apparatus for detecting pressure waves caused by movement of a body organ, muscle group, limb or the like and transmitted through a catheter or lead body to the implanted medical device employing a pressure wave transducer mounted in relation to the proximal end of the catheter or lead to detect the transmitted pressure waves. The system may also include a reference transducer having the same pressure wave response characteristics as the pressure wave transducer but isolated from the proximal connector end for providing a reference signal including common mode pressure wave noise that both transducers are simultaneously subjected to. The pressure wave signal and the reference signal are preferably amplified, bandpass filtered to the body pressure wave of interest and stored, telemetered out or used to trigger a device operation. The pressure and reference wave transducers preferably are piezoelectric crystal transducers or accelerometers in direct or indirect mechanical contact with the proximal connector end of the catheter and is encapsulated from the body within a device connector assembly. Preferably, the catheter is a lead extending into direct or indirect contact with the patient's heart. Cardiac pressure waves and respiration pressure waves are both transmitted proximally through the lead body to the pressure wave transducer. Pressure wave signals may be derived in parallel to detect particular characteristics of the cardiac and/or respiratory cycle to provide timing signal(s) for controlling the device operations.

18 Claims, 6 Drawing Sheets

U.S. PATENT DOCUMENTS

| | | | |
|---|---|---|---|
| 5,103,832 | 4/1992 | Jackson | 128/675 |
| 5,188,078 | 2/1993 | Tamaki . | |
| 5,312,441 | 5/1994 | Mader . | |
| 5,320,643 | 6/1994 | Roline . | |
| 5,324,326 | 6/1994 | Lubin . | |
| 5,331,966 | 7/1994 | Bennett . | |
| 5,342,406 | 8/1994 | Thompson . | |
| 5,353,800 | 10/1994 | Pohndorf et al. | 128/673 |
| 5,535,752 | 7/1996 | Halperin et al. | 128/673 |

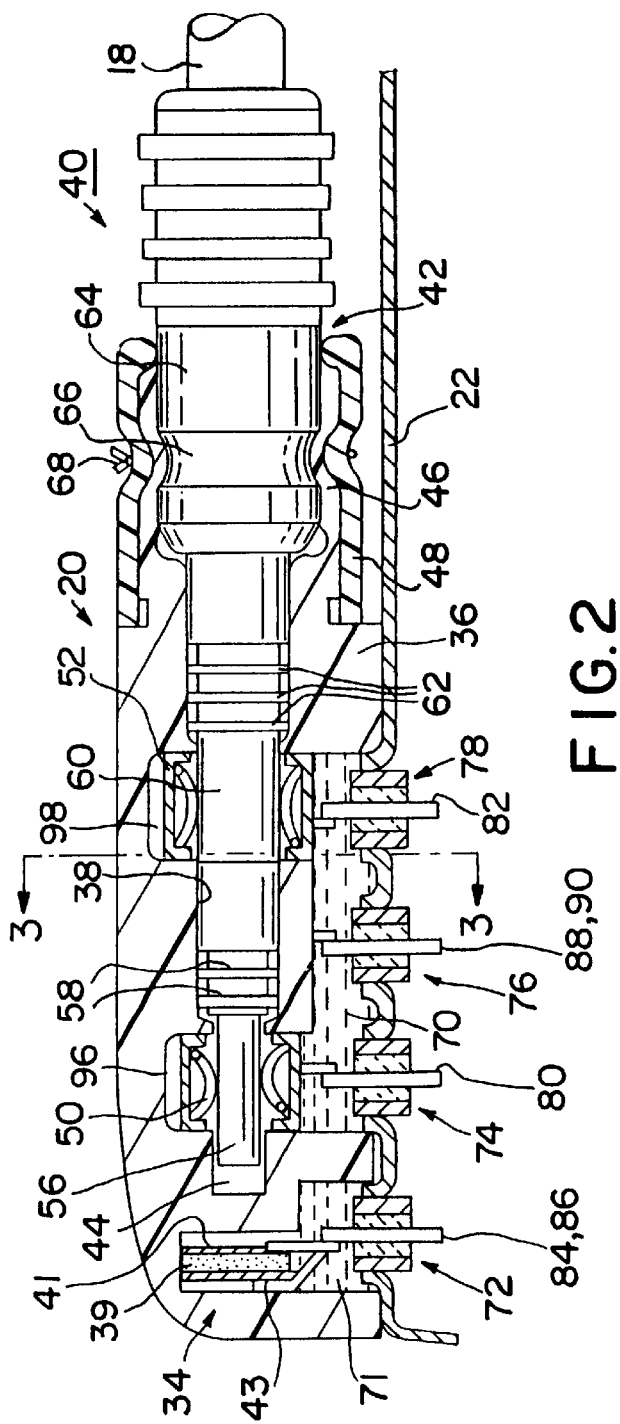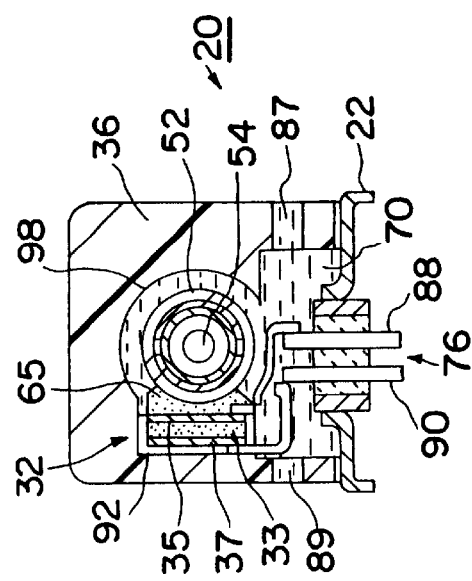
FIG. 2
FIG. 3

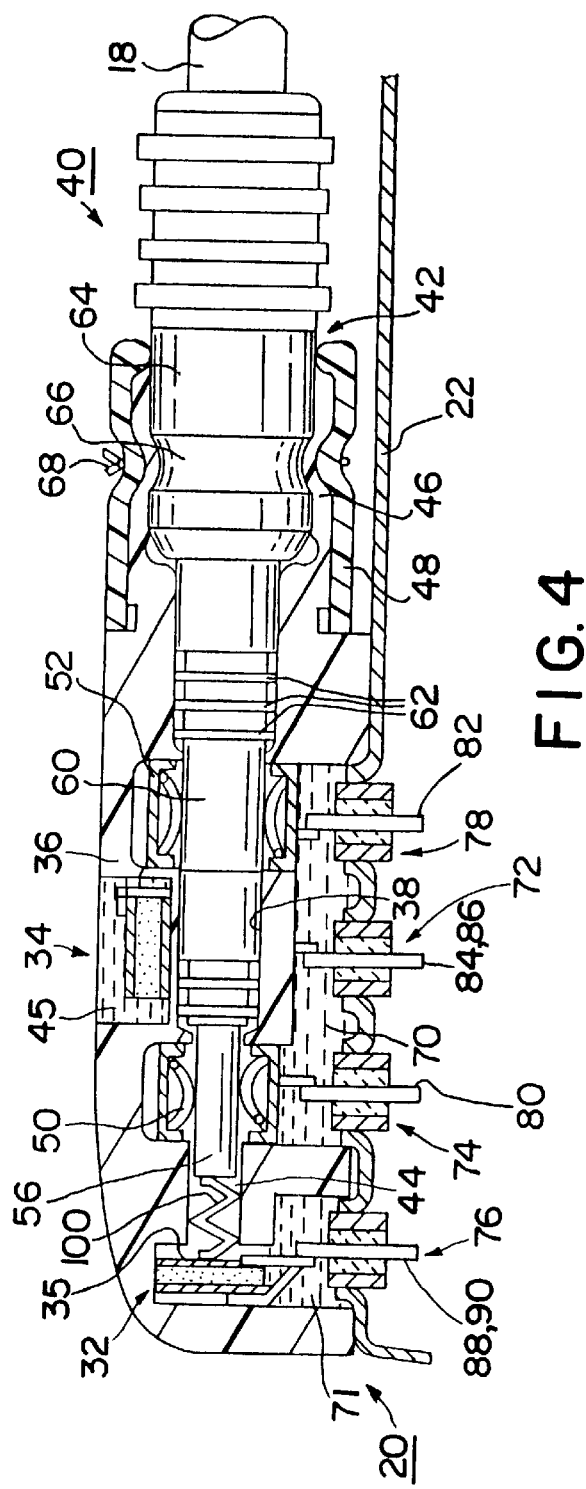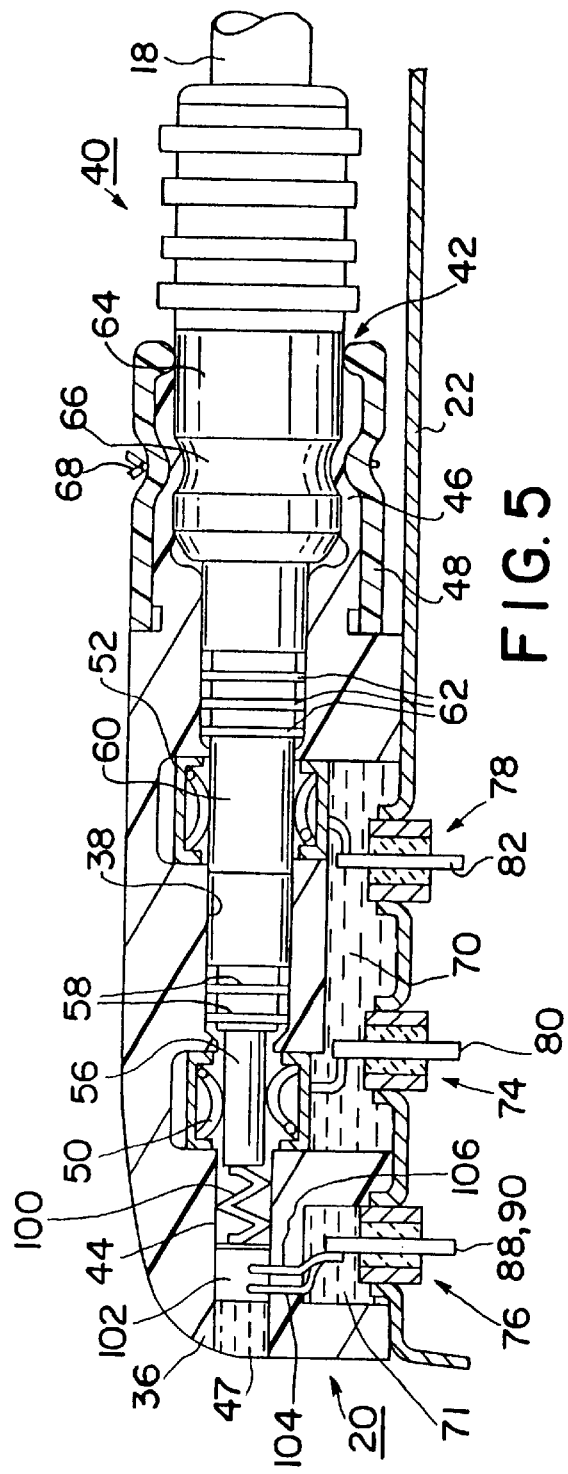

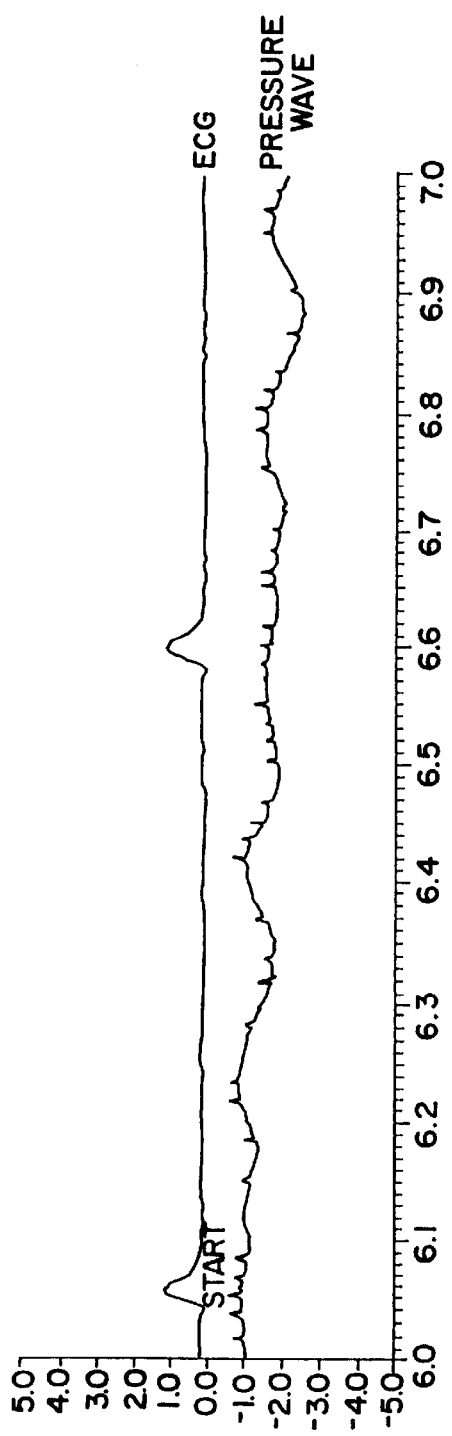
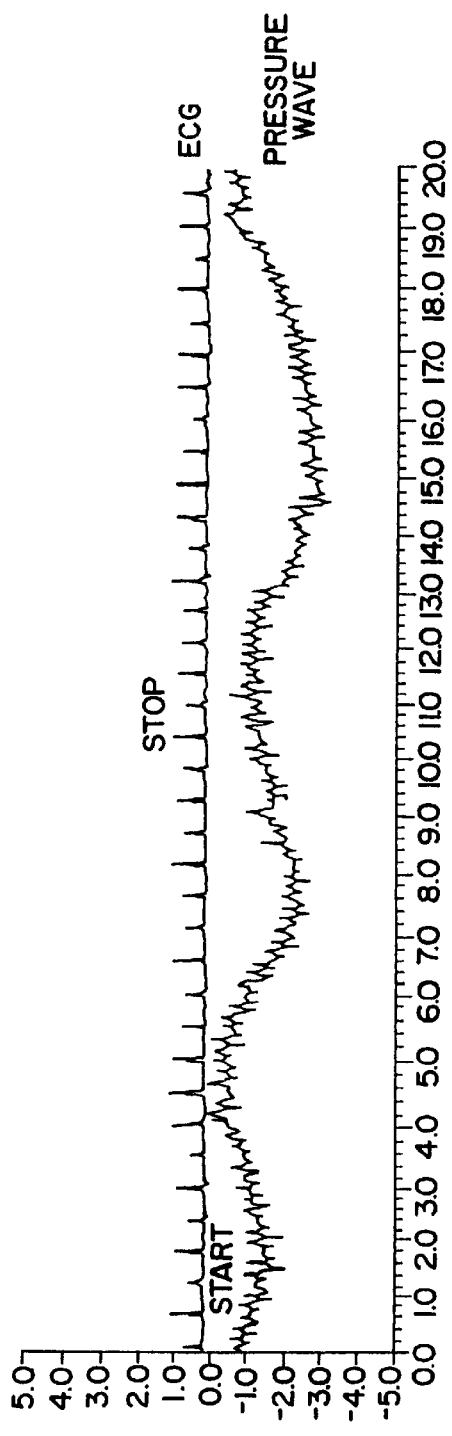

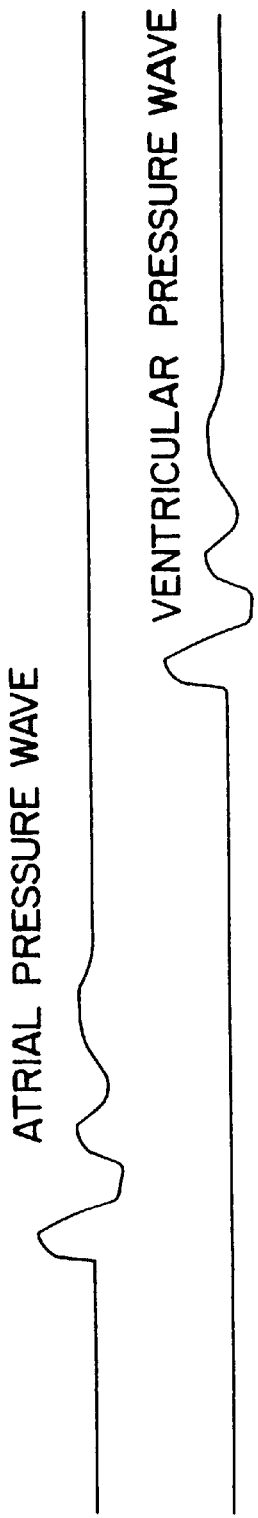
FIG. 9
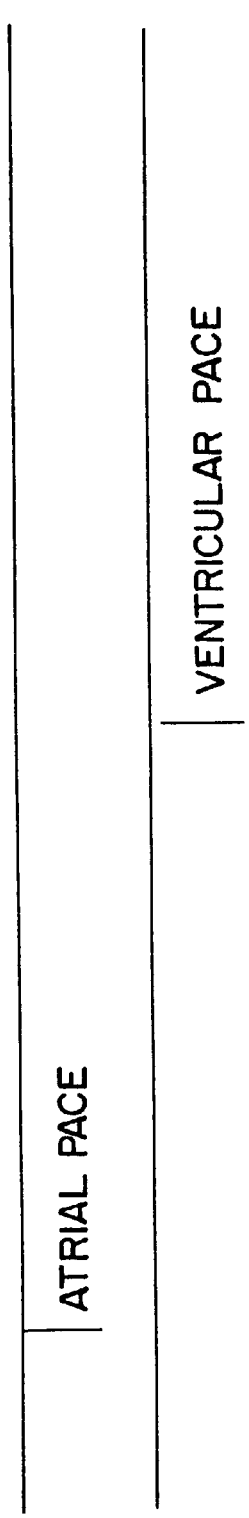
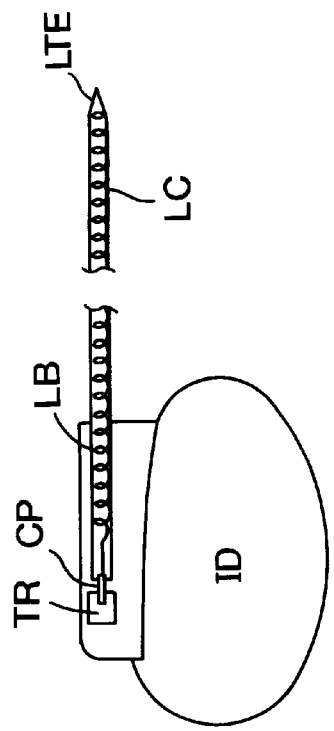
FIG. 10

5,899,927

DETECTION OF PRESSURE WAVES TRANSMITTED THROUGH CATHETER/ LEAD BODY

This application is a continuation of application Ser. No. 08/625,029 filed on Mar. 28, 1996, now abandoned.

CROSS-REFERENCE TO RELATED APPLICATION

Reference is hereby made to commonly assigned U.S. patent application Ser. Nos. (P-4527) filed on even date herewith and entitled VERIFICATION OF CAPTURE USING ACOUSTIC WAVES TRANSMITTED THROUGH PACING LEAD and (P-4528) filed on even date herewith and entitled RATE RESPONSIVE PACEMAKER.

FIELD OF THE INVENTION

The present invention generally relates to implantable medical devices having a catheter or lead in direct or indirect contact with a body organ, muscle group or limb capable of mechanical movement and more particularly to a method and apparatus for detecting pressure waves of mechanical and/or acoustic origin caused by movement of the body organ and propagated by the catheter or lead body to the implanted medical device.

BACKGROUND OF THE INVENTION

Certain organs of the body mechanically expand and contract on a regular basis, most notably the diaphragm and lungs during breathing and the heart as it beats. Muscle groups and body limbs also mechanically expand and contract and move under the control of the central nervous system. When a dysfunction occurs in these body systems, examinations are conducted to determine the nature of the dysfunction and a variety of therapies are prescribed to restore the function. Such examinations include monitoring and the delivery of therapies including drugs and/or electrical stimulation to restore the affected function.

With respect to the heart, the cells of the chambers of the heart relax and contract in an organized and relatively rhythmic cycle due to gradual polarization followed by rapid and organized depolarization of the cardiac cells. The depolarization is accompanied by a relatively forceful contraction of the chamber in a manner described extensively in the literature. Cycles of this type exhibit characteristic electrical signal waveforms of the polarization-depolarization-re-polarization wavefronts referred to as the PQRST electrogram complex. The accompanying relaxation of the heart muscle draws blood into the chambers and the forceful mechanical contraction ejects blood through the valves. The resulting blood pressure waves are audible through the adjacent tissue of the thoracic cavity as a characteristic "lub-dub" sound. In a similar manner, the relaxation and contraction of the diaphragm causes air to be drawn in and ejected from the lungs with a characteristic motion and sound.

For a wide variety of reasons, the detection, display and/or measurement of the electrical signals and the acoustic waves or sounds of these heart and lung cycles have long been of medical interest. In addition, the mechanical motion of the lungs and surrounding thoracic cavity have been the subject of measurement using impedance plethysmography.

Of course, cardiac sounds and the sounds of respiration are commonly listened to by trained medical personnel employing use of passive or active stethoscopes manually positioned over the patient's chest during a medical examination. In this manner, congestion in the lungs, if present, or the characteristic lub-dub sounds of the sequential depolarization of the atria and ventricles of the heart may be listened to. Together with other symptoms, a number of illnesses of the heart and lungs may be diagnosed and treatment prescribed.

Efforts have been underway for many years to develop implantable sensors for temporary or chronic use in a body organ or vessel for a variety of uses, and particularly for measuring aspects of the cardiac and breathing cycles. Catheters and leads are used in conjunction with a wide variety of cardiac medical devices, including implanted and external pacemakers, cardioverter/defibrillators, drug dispensers, cardiac monitors, cardiac assist devices, implanted cardiomyoplasty stimulators, muscle and nerve stimulators, and the like. One or more catheter or lead is attached at the proximal end thereof to a device port or terminal and the distal end segment thereof is introduced into direct contact with the heart muscle or extended within the atrial and/or ventricular heart chamber in contact with blood and in indirect contact with the heart muscle. A condition of the heart or of the blood is sensed and/or a therapy is delivered through the lead or catheter.

For example, a simple cardiac catheter for measuring blood pressure changes includes an elongated catheter body extending between a proximal connector end and a distal end having one or more end openings or a balloon adapted to be introduced into a heart chamber. Drugs or agents may be dispensed through the catheter lumen to a desired location. Blood pressure fluctuations in the column of fluid in the lumen may be measured as long as the distal end opening remains open or the balloon remains capable of flexing with pressure changes. However, unless anticoagulants are continuously dispensed through the catheter lumen, the distal end of the catheter becomes encased in fibrosis interfering with balloon motion and/or closing the end openings within a relatively short time. For this and other reasons, such simple blood pressure measuring catheters cannot be left in place chronically or implanted permanently in association with an implanted medical device.

Catheters have also been proposed including sensors incorporated into the catheter distal tip for measuring various blood parameters. In these cases, the catheter body incorporates electrical conductors and proximal end connector terminals in order to power such sensors and to convey electrical signals from the sensors to an implanted or external medical device.

A lead is a form of a catheter having one or more lead conductors extending between a proximal connector terminal(s) and distal exposed electrode(s) from which electrical stimulation may be delivered or electrical signals of the body may be detected. A pacing lead includes one or more pace/sense electrodes and associated lead conductors. A cardioversion/defibrillation lead includes one or more cardioversion/defibrillation electrodes and associated lead conductors, and may also include one or more pace/sense electrodes and associated lead conductors.

In the context of cardiac pacemakers and/or cardioverter/ defibrillators comprising implantable pulse generators (IPGs) and leads of this type, a variety of indwelling sensors have been proposed in combination with the leads for sensing parameters including blood pressure, the rate of change of blood pressure, blood gas concentrations, blood pH, and blood temperature or for sensing the mechanical motion of the heart. The sensed signals as well as the P-wave and/or R-wave of the heart sensed through the pace/sense electrodes in contact with the patient's atrium and/or ventricle, respectively, are employed for a variety of reasons.

In pacemakers, such indwelling sensors have been proposed for use in algorithms for adjusting the pacing rate to meet the demand for cardiac output as related to a characteristic of the sensed parameter that varies with exercise. Other rate-responsive pacemakers have been widely commercialized employing an IPG mounted piezoelectric crystal sensor responsive to the level of patient activity, referred to as an "activity" sensor. The use of an activity sensor and indwelling sensor or two or more indwelling sensors in combination and the processing of the sensor signals to derive a pacing rate control signal are disclosed, for example, in commonly assigned U.S. Pat. No. 5,188,078.

Still other rate-responsive pacemakers have been commercialized employing impedance variations with respiration as measured between spaced thoracic electrodes as disclosed, for example, in EPO Patent Nos. 0 089 014 and 0 151 689, incorporated herein by reference. The thoracic electrodes may be spaced apart and away from the heart or may include a pacing lead electrode. In the '689 patent, a pacing rate control signal is developed from the variation in the measured impedance as a function of pulmonary minute ventilation.

The use of a variety of sensors in pacemakers is also proposed for detecting capture of the heart by a pacing pulse, i.e., detecting the evoked depolarization in response to preceding pacing pulse. In order to conserve battery power and prolong the life of implanted pacemakers, it is desirable to minimize the energy of the pacing pulse to provide a minimal "safety margin" of the pulse energy over the threshold energy sufficient to capture the heart. The detection of the evoked electrical signal is difficult because the pacemaker sense amplifier is "blinded" by the residual "polarization" energy of the pacing pulse at the sensing electrode for a time period. While the detection of an evoked ventricular depolarization R-wave superimposed on the decaying residual polarization wave may be possible under carefully controlled circumstances, the detection of the much lower amplitude evoked P-wave has not proven possible. Therefore, the alternate use of indwelling sensors of the types described above to detect the change in blood temperature, gas concentration, or pressure accompanying the evoked response has been proposed as described in detail in commonly assigned U.S. Pat. Nos. 5,320,643, 5,331,996 and 5,342,406.

In a further approach, a system disclosed in U.S. Pat. No. 4,114,628 suggests the use of a mechanical heart motion sensor in contact with the heart to detect capture or LOC. The disclosed sensor in the '628 patent is a moving core, coiled wire inductor transducer mounted within an endocardial or epicardial lead coupled to the IPG.

In the context of automatic implantable cardioverter/defibrillators, fibrillation is typically detected by the continuous detection and analysis of features of the P-waves or R-waves, including high rate, rate regularity, sudden onset of high rate, etc. When the atria or ventricles of the heart are in fibrillation, the associated P-waves or R-waves become chaotic, and the heart chamber is unable to vigorously contract in the normal manner. The confirmation of ventricular fibrillation by detecting the absence of blood pressure is proposed in U.S. Reissue Pat. No. Re 27,652. The confirmation of ventricular fibrillation by detecting the absence of heart motion characteristic of normal contractions along with a R-wave high rate has been proposed in U.S. Pat. Nos. 3,815,611 and in the above-referenced '628 patent. The use of the indwelling blood pressure sensors, blood gas concentration sensors or temperature sensors to confirm fibrillation by detecting a change in the measured parameter in conjunction with the high rate P-wave or R-wave is also suggested in the prior art.

Implantable cardiac monitors, e.g. the MEDTRONIC® implantable hemodynamic monitor employ pacing leads attached to the patient's heart for simply monitoring and storing EGM data and an indwelling pressure sensor for developing an absolute pressure signal from the heart. A reference pressure sensor is incorporated into the connector block assembly for detecting ambient atmospheric pressure that is subtracted from the pressure sensor signal to provide the absolute pressure sensor. Patient's suffering from congestive heart failure are candidates for such implantable hemodynamic monitors. Such patient's suffer from episodes of cardiac insufficiency accompanied by labored breathing that is not presently monitored.

The detection of heart sounds rather than the R-wave peak or a pressure sensor signal has also been suggested anonymously in *RESEARCH DISCLOSURE* No. 37150, entitled "Use of Heart Valve Sounds as Input to Cardiac Assist Devices" (March, 1995) for use in controlling operations of pulsatile cardiac assist devices. The listed cardiac assist devices include intra-atrial blood pumps (IABPs), cardiomyoplasty/cardiac assist devices (of the type described in commonly assigned U.S. Pat. No. 5,069,680, for example), aortomyoplasty and ventricular assist devices (VADs). The heart sounds are picked up by a microphone, amplified, bandpass filtered and compared to a "signature" sound pattern to derive a control signal timed to the second or "dub" heart sound, which is related to the dicrotic notch of the aortic pressure wave. No specific structure for accomplishing this is disclosed. In U.S. Pat. No. 4,763,646 to Lekholm, a heart sound detector is also proposed to be mounted in one or more pacing leads arranged in or about the heart or to be mounted in the IPG case for acoustically sensing heart sounds transmitted through a fluid filled lumen. The use of a pressure sensor, microphone or accelerometer is proposed for the heart sound detector.

Despite the prodigious effort expended in developing such indwelling sensors, few have been found to be useful or acceptable for chronic use. Typically, the foreign object body reaction encapsulates the sensor and isolates it from the parameter to be detected and measured. In addition, the active sensors require additional lead conductors and are electrically inefficient. Consequently, such sensors are complex in design, difficult to manufacture, relatively expensive, and short lived.

For example, a great deal of effort has been expended in developing indwelling absolute pressure and pressure rate of change sensors as noted above for measuring these parameters in a heart vessel or chamber. Many designs of such chronically or permanently implantable pressure sensors have been placed in limited clinical use. Piezoelectric crystal or piezoresistive pressure transducers mounted at or near the distal tips of pacing leads, for pacing applications, or catheters for monitoring applications, are described in U.S. Pat. Nos. 4,023,562, 4,407,296, 4,432,372, 4,485,813, 4,858, 615, 4,967,755, and 5,324,326, and in PCT Publication No. WO 94/13200, for example. These sensors and an improved sensor and operating system are described in detail in commonly assigned U.S. patent application Ser. No. 08/394870 filed Feb. 27, 1995, for IMPLANTABLE CAPACITIVE ABSOLUTE PRESSURE AND TEMPERATURE SENSOR and Serial No. 08/394,860 filed Feb. 27, 1995, for IMPLANTABLE CAPACITIVE ABSOLUTE PRESSURE AND TEMPERATURE MONITOR SYSTEM.

Other semiconductor sensors employ CMOS IC technology in the fabrication of pressure responsive silicon diaphragm bearing capacitive plates that are spaced from stationary plates. The change in capacitance due to pressure waves acting on the diaphragm is measured, typically through a bridge circuit, as disclosed, for example, in the article "A Design of Capacitive Pressure Transducer" by Ko et al., in *IEEE Proc. Symp. Biosensors*, 1984, p.32. Again, fabrication for long term implantation and stability is complicated and unproven.

This concentrated focus on the development of accurate, efficient, reliable and permanently implantable, indwelling pressure sensors on lead bodies has taken place in recognition that the detection of pressure waves, particularly in the cardiac and pleural context, has a great number of applications as described above. However, the indwelling pressure sensor approach requires the implantation of the sensor into the heart chamber, where certain sensor types may become fibrosed and lose the ability to respond to mechanical heart motion or blood pressure changes associated with the contraction of the heart chamber or in association with the lungs or diaphragm where fibrosis may also render it ineffective.

In virtually all approaches, it is necessary to rely on additional components and circuitry which consume more energy, require additional lead conductors, increase the bulk and cost of the system, increase the cost of the implantation, and raise reliability issues. The additional components and circuitry are increased further in dual chamber pacemakers. Very few of the numerous approaches of the prior art have been attempted in an implantable pacemaker system and fewer yet have been proven clinically useful and commercially successful.

Therefore, despite the considerable effort that has been expended in designing such sensors, a need exists for a body implantable, durable, long-lived and low power sensor for accurately sensing pressure waves and related parameters in the body over many years of implantation.

SUMMARY OF THE INVENTION

Accordingly, it is an object of the present invention to provide a practical and durable substitute for an indwelling sensor particularly for measuring pressure waves at a site of interest in a patient's body.

It is a further object of the present invention to employ the lead or catheter body to convey pressure waves from the site of interest remotely to a low power pressure wave transducer in contact therewith.

These and other objects of the invention are realized in a system for detecting pressure waves emanating from a site in the patient's body through a catheter extending to the site for use in diagnosing a body function or timing a medical device operation comprising: a catheter having an elongated catheter body extending between a proximal connector end and a distal end adapted to be placed at the site such that a pressure wave is transmitted through said catheter body in response to a body function; a connector assembly for attachment with said proximal connector end; a pressure wave detection transducer mounted in said connector assembly in operative relation with said proximal connector end for detecting said pressure wave and providing a pressure wave signal representative thereof; and means for processing the pressure wave signal for use in an operation of the medical device.

The pressure wave signal is preferably amplified, bandpass filtered to the pressure wave of interest and used to trigger a device operation. The system may also include a reference transducer having the same pressure wave response characteristics as the pressure wave transducer but isolated from the proximal connector end for providing a reference signal including common mode pressure wave noise that both transducers are simultaneously subjected to. The reference signal is also amplified, bandpass filtered to the pressure wave of interest and subtracted from the pressure wave signal to eliminate the common mode pressure wave noise component. The resulting signal is employed to trigger the desired device action.

The pressure wave transducer and the reference transducer (if present) are preferably a piezoelectric crystal transducer, a pressure sensor or an accelerometer in direct or indirect mechanical contact with the proximal connector end of the catheter. Preferably, the pressure wave and reference transducers are of the same type and have the same characteristics and specifications. Any transducer can be used, including resonant micro beams, piezoresistive diaphragms etc., so long as they are of sufficient sensitivity and responsive to the appropriate frequency passage.

The pressure wave transducer is preferably encapsulated within the connector assembly in a position making contact with the lead body through a connector element. The reference transducer, when present, is preferably also encapsulated from the body within the connector assembly away from direct or indirect coupling with the lead connector end and aligned in parallel with the pressure wave transducer. The reference transducer may alternatively located elsewhere in the implantable medical device.

Preferably, the catheter is a electrically conducting lead extending into direct or indirect contact with the patient's heart, organ, or muscle of interest, and the system comprises an implanted medical device of the types described above coupled to the proximal connector end of the lead. In the context of a cardiac monitor or IPG, cardiac pressure waves and respiration pressure waves are both transmitted proximally through the lead body to the pressure wave transducer. The cardiac pressure waves are caused by the change in blood pressure or direct mechanical motion of the heart, e.g. the opening and closing of a heart valve, against the distal end segment of the lead. The cardiac pressure wave therefore reflects a heart sound and/or mechanical shock originating in the heart. The respiration pressure waves are caused by mechanical motion of the lungs transmitted to the heart and thoracic cavity during the respiratory cycle. Either or both pressure wave signals may be derived in parallel to detect particular characteristics of the cardiac and/or respiratory cycle for monitoring the cardiac and/or respiratory cycles or to provide timing signal(s) for controlling the device operations described above. It is believed that any of the commonly used leads for pacemakers can perform satisfactorily for this invention.

The present invention advantageously provides the ability to reliably provide timing signals for a wide variety of applications described above without having to solve the problems associated with directly exposing a sensor, particularly a pressure or motion sensor, to the hostile environment of the body and without having to provide additional conductors in the lead body.

The present invention may be of use with catheters, but is of particular advantage in use with leads of the types described above. In particular, pacing leads have been implanted for many years in a large number of patient's hearts in the context of pacemaker and pacemaker-cardioverter-defibrillator IPG's. Such IPG's may be replaced with IPG's constructed in accordance with the present invention having the improved capabilities and features thereof without having to replace the leads with sensor bearing leads, resulting in a considerable savings and while providing improved patient treatment.

Moreover, the invention may also be used advantageously in conjunction with indwelling leads or catheters coupled to external medical devices.

BRIEF DESCRIPTION OF THE DRAWINGS

Other objects, advantages and features of the present invention will be readily appreciated as the same becomes better understood by reference to the following detailed description when considered in connection with the accompanying drawings, in which like reference numerals designate like parts throughout the figures thereof and wherein:

FIG. 2 is a side cross-section view of a lead connector assembly taken along lines 2—2 of FIG. 1 within which at least a piezoelectric crystal pressure wave transducer and a reference transducer are incorporated in relation to the lead proximal connector end in accordance with a first embodiment of the invention;

FIG. 3 is an end cross-section view taken along lines 3—3 of the connector assembly of FIG. 2;

FIG. 4 is a side cross-section view of a lead connector assembly also taken along lines 3—3 of FIG. 1 within which at least a piezoelectric pressure wave transducer and a reference transducer are incorporated in relation to the lead proximal connector end in accordance with a second embodiment of the invention;

FIG. 5 is a side cross-section view of a lead connector assembly also taken along lines 3—3 of FIG. 1 within which an accelerometer pressure wave transducer is incorporated in in-line indirect mechanical contact the lead proximal connector end in accordance with a third embodiment of the invention;

FIG. 7 is a waveform diagram depicting the cardiac cycle pressure wave detected by the pressure wave transducer in relation to the preceding intrinsic PQRST complex;

FIG. 8 is a waveform diagram depicting the respiration cycle pressure wave detected by the pressure wave transducer in relation to a series of intrinsic PQRST complexes; and FIG. 9 is a waveform diagram depicting the cardiac cycle pressure wave detected by the pressure wave transducer in relation to a preceding pace pulse.

DETAILED DESCRIPTION OF THE PREFERRED EMBODIMENTS

The preferred embodiment of the invention is illustrated in the context of a connector block for an implantable patient monitor, e.g. the MEDTRONIC® implantable hemodynamic monitor, or an IPG, e.g. an implantable pacemaker IPG of the type described in detail in the above-referenced '078 and '406 patents or an implantable pacemaker-cardioverter-defibrillator IPG of the type described in commonly assigned U.S. Pat. No. 5,312,441, all incorporated herein by reference in their entireties. In such monitors and IPGs, the connector assembly is molded as a separate piece part and attached to the hermetically sealed case or can for the power source and electronic components in a manner shown, for example, in commonly assigned U.S. Pat. No. 5,070,605, incorporated herein by reference.

Figure 1:
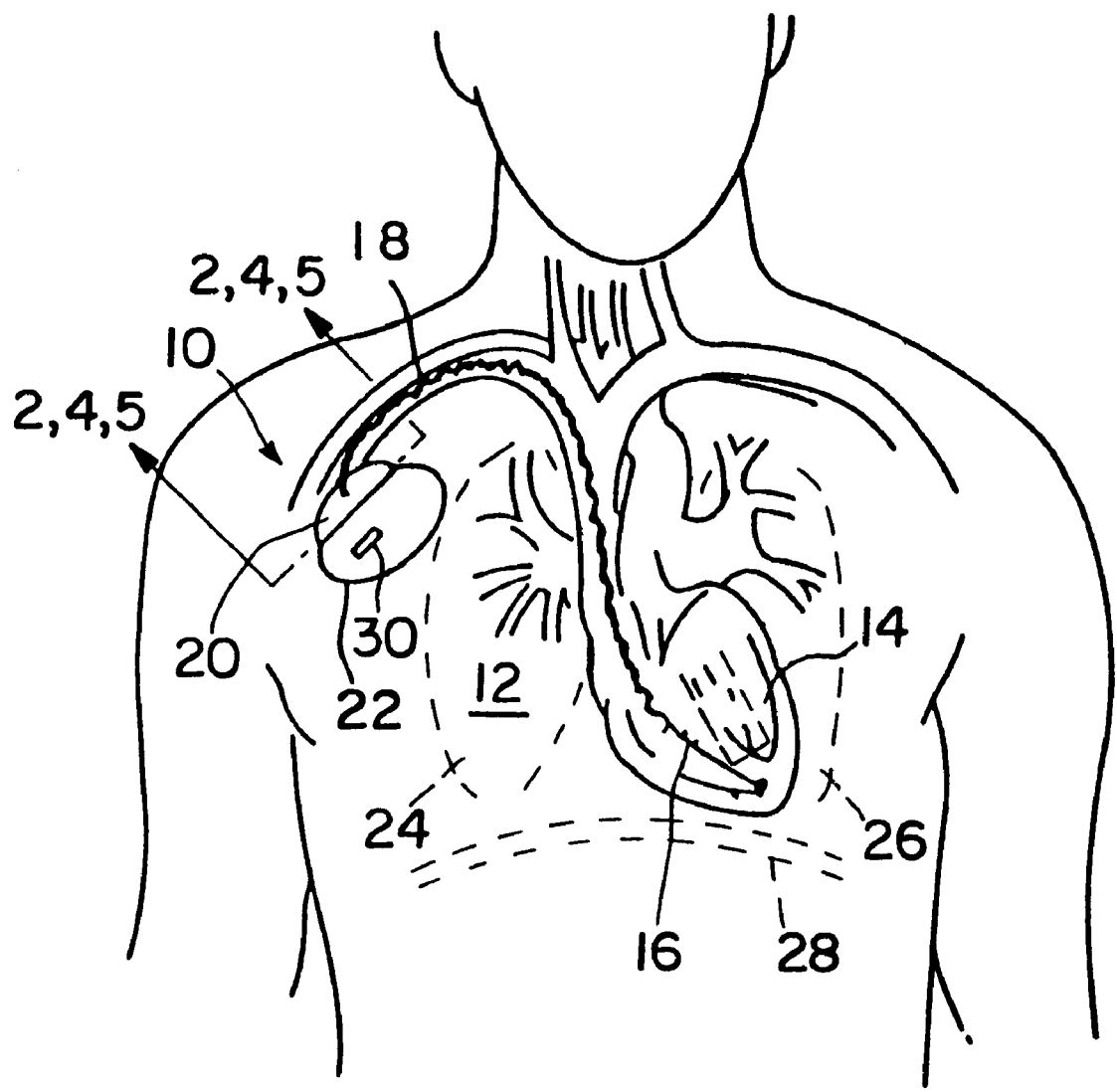
FIG. 1 is a schematic illustration of an IPG or monitor implanted in a patient's chest and an endocardial lead transvenously introduced into the heart and traversing the patient's chest.

FIG. 1 is a schematic illustration of such an IPG or monitor 10 implanted in a patient's chest 12 and an endocardial lead 18 (or leads) transvenously introduced into the heart 14 and traversing the patient's chest 12. The IPG or monitor 10 includes the connector assembly 20 and the case or can 22 enclosing the power supply and circuitry. As the heart 14 contracts and expands, it creates pressure waves which are transmitted into the distal end segment 16 of lead 18 and are conducted proximally to the relatively still IPG or monitor 10. Similarly, as the lungs 24, 26 expand and contract the pleural cavity and chest with the respiration cycle controlled by the diaphragm 28, the chest movement creates pressure waves that impart movement to the elongated lead 18 and are conducted proximally to the relatively still IPG or monitor 10.

Since the lead distal end segment 16 is typically firmly attached to the heart 14 (and may in fact be alternatively attached to the epicardium) so that good electrical contact is maintained, the cardiac contraction pressure wave may constitute a reaction to a physical shock, i.e. a rapid mechanical movement, imparted to the distal end segment of the relatively forceful contraction of the heart. The transmitted cardiac contraction pressure wave may comprise the mechanical movement itself effecting an acoustic or ringing response of the lead body and may include a component of the actual cardiac contraction sound, and we define it as such.

We have discovered that the cardiac contraction pressure wave may be transmitted through the solid lead body and readily detected at the proximal connector end of the lead 18 by a sensor in direct or indirect mechanical contact with the lead body. Similarly, we have discovered that the respiratory pressure wave, which is more gradual and primarily attributable to mechanical motion of the lead body may also be readily detected at the proximal connector end of the lead 18. This discovery allows the replacement of sensors in the distal tip segment of a lead or catheter, which suffer the deficiencies detailed above, with sensors associated with the lead's proximal connector end, preferably in the connector block assembly of the implanted device. The principles of the invention illustrated in the following preferred embodiments are also applicable to detection of pressure waves originating in other organs, muscles, muscle groups or limbs conveyed through catheters or leads to the pressure wave sensor in the medical device.

FIGS. 2 and 3 depict the lead connector module or assembly 20 coupled with a proximal connector end 40 of a lead 18 and the incorporation of a pressure wave transducer 32 and a reference transducer 34 in accordance with a first embodiment of the invention. Although a specific connector block and lead type are illustrated in the figures, it will be understood that the invention may be practiced with any lead configuration having in-line or bifurcated lead proximal connector ends and connector assembly configurations for such lead connector ends.

In this first embodiment, the transducers 32 and 34 are each formed of a piezoelectric crystal of the type employed as an activity sensor in commercially available MEDTRONIC® THERA® DR IPGs for rate-responsive pacing in the DDDR mode and other modes. In FIG. 1, such an activity sensor 30 is depicted adhered within the can 22. Such transducers 32, 34 are formed of a rectangular piezoelectric crystal of about 0.250×0.125×0.022 inches which is reduced in size from the activity sensor. The major opposed surfaces of the piezoelectric crystal 33 are coated with thin film electrodes 35 and 37, and the major opposed surfaces of the piezoelectric crystal 39 are coated with thin film electrodes 41 and 43 that are electrically attached to sensor lead wires as described below. The resulting capacitive transducer provides an electrical output signal on the sensor lead wires that varies in amplitude in response to minute deflections of the piezoelectric crystal in response to the acoustically or mechanically conducted cardiac and respiratory pressure waves.

It should be noted that the orientation of the reference transducer 34 should be in a parallel plane with plane of the pressure wave transducer 32, rather than in a transverse plane as depicted for convenience of illustration in the FIGS. 2 and 3. The parallel orientation provides a more exact response of both transducers to common mode noise originating elsewhere in the body, for example.

Figure 6:
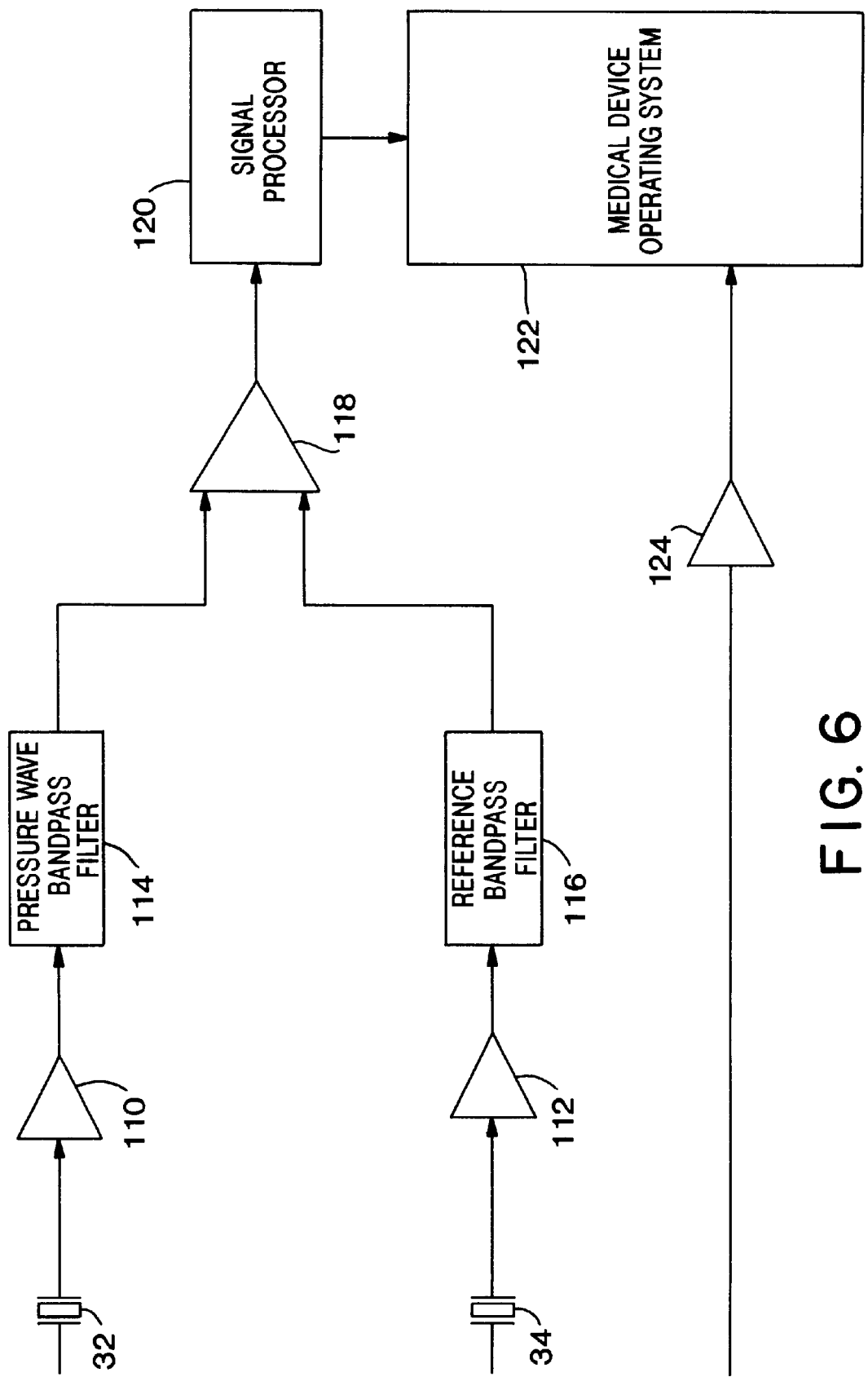
FIG. 6 is a block diagram of a signal processing system for processing the pressure wave and reference signals from the pressure wave transducers and reference transducers.

The connector assembly 20 shown in FIGS. 2 and 3 is similar to that described and shown in FIGS. 4–6 of the above-incorporated '605 patent. In particular, the connector 20 is formed of a connector housing 36 of uncolored, transparent epoxy molded to form an elongated, lead connector end bore 38 open at the tubular end 42 and terminating in a pin receptacle chamber 44. The connector housing 36 also encloses the transducers 32, 34, feedthrough terminal pins identified below and in-line lead retainers 50 and 52 described below. A flexible sleeve 48 fits over tubular end extension 46.

The bore 38 is shaped to receive the proximal connector end 40 of in-line, bipolar lead 18. The lead 18 is typically constructed of coaxially arranged and electrically insulated coiled wire conductors extending the length of an outer insulating sheath and forming the lead body surrounding a lumen 54 but may be constructed without a lumen. The proximal connector end 40 conforms to the IS-1 standard for bipolar in-line lead connectors and includes a proximal connector pin 56 coupled to the inner coiled wire conductor and sized to fit within the pin engaging, deflectable beam, cylindrical lead retainer 50. An insulating sheath overlies the junction of the connector pin 56 and the inner coiled wire conductor and is formed with annular moisture sealing ribs 58 that engage the walls of the bore 38.

A connector ring 60 is coupled to the outer coiled wire conductor (not shown) and sized to fit within the pin engaging, deflectable beam, lead retainer 52. An insulating sheath overlies the junction of the connector ring 60 and the outer coiled wire conductor and is formed with further annular moisture sealing ribs 62 that engage the walls of the bore 38.

The lead connector end 40 is enlarged to a diameter 64 distally to the connector ring 60 and has an annular groove 66 in diameter 64 shaped to be retained in a necked down annular portion of the tubular end extension 46. The attachment of the lead connector end 40 in the bore 18 may be secured by a suture ring 68. The secure electrical connection of the connector pin 56 with the electrically conductive lead retainer 50 and the connector ring 60 with the electrically conductive lead retainer 52 is described in detail in the above-incorporated '605 patent.

A series of electrical feedthroughs 72, 74, 76, 78 are mounted to extend through the mating surface of the can 22 and into cavities 70 or 71 (preferably minimized into channels) sealed with medical grade silicone rubber adhesive or the like when the connector assembly 20 is attached to the can 22. Lead feedthrough pins 80 and 82 extend through the lead feedthroughs 74 and 78, respectively and are electrically connected to the lead retainers 50 and 52, respectively, by short wire conductors. Reference feedthrough pins 84 and 86 extend through double pin, reference feedthrough 72 and are electrically connected with the thin film electrodes 41 and 43, respectively, of the reference transducer 34 by short transducer wire conductors. Similarly, pressure wave feedthrough pins 88 and 90 extend through double pin, pressure wave feedthrough 76 and are electrically connected with the thin film electrodes 35 and 37, respectively, of pressure wave transducer 32 by short transducer wire conductors. Double pin transducer feedthroughs 72 and 76 may be employed because of the extremely low voltage and current signals generated by the pressure and reference wave transducers 32 and 34.

The connector assembly may be fabricated in one way by positioning the pressure and reference wave transducers 32, 34 and attached wires within opening 92 of cavity 70 and within cavity 71, respectively, and positioning the lead retainers 50 and 52 and attaching wires in the depicted enlarged open portions 96 and 98 of bore 38. The inserted components can then be fixed and sealed from the environment in those positions with silicone rubber adhesive while leaving the ends of the wires exposed for attachment to feedthrough pins. The backfilling of the gap between the pressure wave transducer 32 and the outer surface of the retainer 52 with silicone adhesive ensures that a direct mechanical contact is made with the lead retainer 52 and indirect contact is made with the lead body. Care must be taken to avoid entraining air bubbles in the backfilled silicone rubber adhesive insulating layer between the lead retainer 52 side wall and the adjacent conductive thin film electrode 35.

Alternatively as shown in FIG. 3, the pressure wave transducer 32 is carefully spaced from the lead retainer 52 by an electrical insulating layer 35 to prevent it from contacting the thin film electrode 35 while ensuring indirect contact through the lead retainer 52 to the lead body. In practice, the insulating layer 35 may be a more rigid plastic adhesive for adhering the lead retainer 52 and pressure wave transducer 32 (and associated sensor and retainer leads) together as a sub-assembly that is inserted into the open portion 98 before it is backfilled.

A further alternative approach providing direct contact of the lead retainer 52 with the piezoelectric crystal 33 can be practiced if the two electrodes are deposited on the side where electrode 37 is depicted. Intimate direct contact between the pressure wave transducer 32 and the lead retainer 52 can also be achieved by a thin layer of adhesive at the contact line.

In any case, the connector housing 36 may be formed with welding access ports through which a welding probe may be introduced to weld the conductor wire ends to the feedthrough pins as exemplified by welding ports 87 and 89 shown in FIG. 3. In this final assembly process, the connector assembly 20 is secured to the mating surface of can 22, and the conductor wire ends are welded to the feedthrough pins through the welding access ports. Then, the interior spaces 70, 71 (or channels) and the access ports are backfilled with medical grade silicone rubber adhesive.

The resulting connector assembly 20 of the first embodiment therefore includes a pressure wave transducer 32 that makes direct mechanical contact with the lead 18 and an reference transducer that is isolated from the lead 18 but subjected to common mode noise sources at the location of the monitor or IPG. For example, such common mode noise sources may include pressure waves induced by body or limb movement, speech, coughing, snoring, footfalls and extraneous ambient noise.

Turning to FIG. 4, it depicts and alternative arrangement of the locations of the piezoelectric crystal pressure wave transducer 32 and reference transducer 34. This orientation allows the direct conduction of mechanical pressure wave energy in the pressure wave conveyed up the lead lumen 54 to deflect the piezoelectric crystal 33. The pressure wave transducer 32 is in direct axial alignment with the lead connector pin and mechanically coupled to it by a flexible spacer. e.g. a leaf spring 100. The leaf spring 100 is maintained in the end of the bore chamber 44 so that mechanical contact with the lead connector pin 56 may be maintained given lead and connector fit tolerances. As shown, the chamber 44 is extended to the thin film electrode 35, and the non-conductive leaf spring 100 fits in that space. A conductive leaf spring 100 may be used in a monitor or if the thin film electrode 35 is insulated or if the electrode 33 is located alongside electrode 35. All other aspects of the fabrication of the connector assembly 20 of FIG. 4 are similar to those described above.

The reference transducer 34 is located in a cavity 45 in molded housing 36 that is separated from the lead bore 38 by an internal wall of molded housing 36. Channels are also formed in the molded housing 36 to direct the transducer conductors to the reference feedthrough pins 84, 86. After the reference transducer 34 is positioned in the cavity 45, it is backfilled with silicone rubber adhesive.

In these embodiments of FIGS. 1–4, the placements of the reference transducer 34 and the related conductors and feedthrough 72 are arbitrarily depicted. They may be situated in the connector housing 36 at any convenient location that provides isolation from the pressure wave conducted up the lead 18. The preferred location and orientation of the reference transducer 34 and its related components is in a parallel plane to the plane of the pressure wave transducer 32. In an alternative embodiment, it is possible to eliminate the reference transducer 34 and associated components and employ the signals provided by the activity sensor 30 as reference signals for eliminating common mode noise.

The pressure wave transducer 32 may also be placed at any convenient angle to either of the lead retainers 50 and 52. Moreover, although a single channel monitor or IPG 10 is depicted for the sake of simplicity, it will be understood that the same approaches may be taken to provide a second pressure wave transducer in relation to a second lead for a dual chamber monitor or IPG of the types incorporated above.

In addition, although piezoelectric crystal transducers of the type described are preferred due to their low cost, reliability, low current drain and responsiveness to pressure waves of the type described, piezoelectric crystal moving beam accelerometers may also be used. Other solid state, micro-miniaturized IC accelerometers and transducers may be substituted for the piezoelectric crystal transducers, including miniature IC beam accelerometers and capacitive accelerometers.

Turning now to FIG. 5, it depicts a further embodiment of the invention employing a micro-miniaturized, accelerometer 102 mounted in alignment with the lead connector pin 56 and in indirect contact therewith through a leaf spring 100. Such accelerometers are typically mounted on a diaphragm, and motion of the diaphragm effects motion of the moving element of the accelerometer.

The accelerometer 102 is inserted into the chamber 44 through an access port 47 in molded housing 36 that is backfilled with silicone rubber adhesive. The accelerometer leads 104, 106 are routed to pressure wave feedthrough pins 88, 90 of the pressure wave feedthrough 76. A reference accelerometer isolated from the pressure wave sensing accelerometer may also be provided in the embodiment of FIG. 5 in the same manner as the reference transducer 34 of FIGS. 2–4. All other aspects of the fabrication of the connector assembly 20 of FIG. 5 and its attachment to the can 22 are similar to those described above.

Although the embodiments depicted in FIGS. 1–5 and described above employ leads in relation to monitoring the cardiac cycle and/or the respiratory cycle, it will be understood that implantable monitors and IPGs are used in a wide variety of contexts. A number of other organ and muscle stimulators have been developed to effect the contraction of a stimulated organ, muscle, muscle group or limb and monitors have been developed to detect the intrinsic contractions or motions thereof.

It will also be understood that the present invention may be implemented in catheters used chronically with implantable drug dispensers for monitoring the cardiac cycle, the respiratory cycle or any other motion of an organ, limb or muscle group related to the operation of the drug dispenser.

Turning now to FIG. 6, it is a block diagram of a signal processing system for processing the pressure wave and reference signals developed by the pressure wave transducer 32 and the reference transducer 34 (if present) in the above described IPG or implantable monitor embodiments or in any alternative medical device embodiment using a catheter or lead as described above. The pressure wave and reference signals are first amplified in amplifiers 110 and 112, respectively. The amplified pressure wave and reference signals are then bandpass filtered in bandpass filters 114 and 116, respectively. Then, the amplified and filtered reference signal is subtracted from the amplified and filtered pressure wave signal in differential amplifier 118. The resulting signal is applied to the signal processor 120 of the operating system 122 of interest. The operating system 122 may be microcomputer based IPG, implantable monitor or any other medical equipment that the lead or catheter is coupled to.

In the context of an implantable monitor or an IPG, an additional sense amplifier 124 is coupled to the lead feedthrough pins 80 and 82 for providing a electrical sense signal to the operating system in a manner well known in the art. In cardiac medical device applications, the electrical sense signal may be the electrogram of the patient's heart detected through the lead 18.

The bandpass filter characteristics are tailored to pass the range of amplified signal frequencies of interest and to reject frequency components in the signals that are outside that range. For example, the piezoelectric transducers as described above are sensitive to heart sound or motion frequencies of interest as well as to footfalls when the patient is ambulatory, muscle artifacts or myopotentials associated with limb movements and exercise, and may be responsive to speech and exterior environmental noise. These may constitute "noise" that are first filtered out to the extent possible and then subtracted in differential amplifier 118 to derive the signal of interest. Moreover, increased signal-to-noise performance may be obtained by gating (time windowing) the output signal of differential amplifier 118 inside signal processor 120 to a particular time of interest in any given cycle.

In accordance with the present invention, parallel signal processing channels for deriving multiple signals responsive to each of these sources may be provided in the same system. For example, the atrial and ventricular contractions of the heart, the respiratory cycle and the patient activity level related to the patient's ambulatory rate may all be derived form the pressure wave signal and the reference signal (if present) in parallel signal processing circuits of FIG. 6.

In either case, the frequency range of the bandpass filters for each such channel is selected for the signal to be derived. In sensing cardiac sounds and motion components of the pressure wave, the frequency range of interest is believed to be between about 0.5–7.0 Hz in the atrium and in the ventricle but may be a different range depending on the waveform characteristic to be measured. To sense patient activity related to ambulatory movement, i.e., footfalls the frequency range of interest representing footfalls is between about 0.5–15 Hz. To detect the amplitude and frequency of the respiratory cycle, the frequency range of interest is about 0.05–0.8 Hz.

FIG. 7 is a two second waveform diagram depicting the cardiac cycle pressure wave detected by the pressure wave transducer in relation to the preceding intrinsic PQRST complex as detected from the pressure wave transmitted through a conventional pacing lead implanted in the ventricle of a healthy dog. In this experiment, a wide bandpass filter was employed, and only the pressure wave transducer of the embodiment of FIGS. 2 and 3 was used. FIG. 9 is an idealized waveform diagram depicting the cardiac cycle pressure wave that would be detected by the pressure wave transducer in relation to a cardiac depolarization evoked by a preceding pace pulse.

A lag between the peaks of the PQRST complex and the peaks of the double pulses is observed that is greater than the lag observed between the PQRST peaks and the peaks of the lub-dub sound waves observed using conventional chest electrodes and sound transducers as illustrated in the above-cited *RESEARCH DISCLOSURE* No. 37150. The peaks of FIG. 7 may represent the pressure waveform of the ventricles in forcefully contracting and expelling blood and then relaxing and filling with blood that takes place in closer timed relation to the PQRST complex. A clear correlation between the double signal peaks of the pressure wave and the PQRST complex is observed. This correlation is effective with either an intrinsic depolarization or an evoked depolarization of the heart and in both the atrial and ventricular heart chambers.

FIG. 8 is a 20 second waveform diagram depicting the respiration cycle pressure wave detected by the pressure wave transducer in relation to a series of PQRST complexes in the same dog experiment. The respiration cycle is much longer than the cardiac cycle. Pulmonary minute ventilation may be determined from the amplitude of the peaks of the respiratory cycle and the interval between peaks in a manner well known in the art.

While there has been shown what are considered to be the preferred embodiments of the invention, it will be manifest that many changes and modifications may be made therein without departing from the essential spirit of the invention. It is intended, therefore, in the following claims to cover all such changes and modifications as may fall within the true scope of the invention.

PARTS LIST FOR FIGS. 1–9

IPG or monitor 10
patient's chest 12
heart 14
distal end segment 16
endocardial lead 18
connector assembly 20
case or can 22
lungs 24, 26
diaphragm 28
activity sensor 30
pressure wave transducer 32
piezoelectric crystal 33, 39
reference transducer 34
thin film electrode 35, 37, 41, 43
connector housing 36
lead connector end bore 38
proximal connector end 40
tubular end 42
pin receptacle chamber 44
cavity 45
tubular end extension 46
access port 47
flexible sleeve 48
in-line lead retainers 50, 52
lumen 54
proximal connector pin 56
annular moisture sealing ribs 58
connector ring 60
annular moisture sealing ribs 62
diameter 64
insulating layer 65
annular groove 66
suture ring 68
cavities 70, 71
double pin reference feedthrough 72
lead feedthrough 74, 78
double pin pressure wave feedthrough 76
lead feedthrough pin 80, 82
reference feedthrough pin 84, 86
welding ports 87 and 89
pressure wave feedthrough pin 88, 90
opening 92
enlarged section 96, 98
leaf spring 100
accelerometer 102
accelerometer leads 104, 106
amplifier 110, 112
bandpass filter 114, 116
differential amplifier 118
signal processor 120
operating system 122
sense amplifier 124

We claim:

1. An implantable medical device having a system comprising detecting and processing electronic circuitry housed therein for detecting pressure waves emanating from a site in the patient's body through a catheter extending to the site for use in measuring a body function or modifying the operation of said implantable medical device and wherein said device is connected to said catheter having an elongate body extending between a proximal connector end which is connected to said device and a distal end comprised of non-fluid but flexible materials adapted to be placed at said body site so that a pressure wave at the body site is transmitted through said catheter body in response to a body function; by a connector assembly of the implanted medical device for attachment with said catheter proximal connector end; said system further characterized by having:

a pressure wave transducer mounted in said connector assembly so as to be in operative relation with a non fluid portion of said proximal connector end for detecting said pressure wave and providing a pressure wave signal representative thereof to said implantable medical device.

2. The system of claim 1 further comprising:

a reference transducer mounted in said implantable medical device and isolated from said catheter proximal connector end for detecting common mode pressure wave noise signals and providing a reference signal in response thereto; and signal processing means for processing said reference signal and said pressure wave signal so as to remove said common mode noise and thereby improve said pressure wave signal to better detect pressure waves associated with said catheter distal end body site.

3. The system of claim 2 wherein said reference to transducer is mounted in said connector assembly.

4. The system of claim 1 wherein said pressure wave detection transducer is mounted in said connector assembly in mechanically linked contact with said proximal connector end.

5. The system of claim 4 wherein said pressure wave detection transducer is a piezoelectric crystal transducer adapted to be deflected by pressure waves traveling through said catheter body to said proximal connector end and by physical vibration of said proximal connector end.

6. The system of claim 5 wherein:

said connector assembly includes a connector bore for receiving and attaching with said proximal connector end by the insertion of said proximal connector end; and said piezoelectric crystal transducer is mounted alongside said connector bore for physical contact with said proximal connector end upon its insert ion into said connector bore.

7. The system of claim 1 wherein said catheter includes an electrical conductor extending between said proximal connector end and said distal end thereof.

8. The system of claim 7 further comprising:

a reference transducer mounted in said connector assembly and isolated from said proximal connector end for detecting common mode noise signals and providing a reference signal in response thereto; and means for processing said reference signal and said pressure wave signal for removing common made noise and detecting pressure waves associated with said body site.

9. The system of claim 1 wherein:

said connector assembly includes a connector bore for receiving and attaching with said proximal connector end; and said pressure wave transducer is mounted alongside said connector bore for physical contact when said proximal connector end is inserted into said connector bore.

10. The system of claim 9 wherein said pressure wave detection transducer is a piezoelectric crystal transducer.

11. The system of claim 1 wherein said pressure wave detection transducer is a piezoelectric crystal transducer.

12. An implantable medical device, having a system comprising detecting and processing electronic circuitry housed therein for detecting pressure waves emanating from a site in the patient's body through a catheter extending to the site for use in making measurements of a body function so as to enable modifying the operation of said medical device at least in part based on said measurements comprising:

a catheter having an elongate non-liquid body extending between a proximal connector end and a distal end adapted to be placed at said body site so that a pressure wave at the body site is transmitted through said catheter body in response to a body function;

a connector assembly of the implanted medical device for attachment with said proximal connector end;

a pressure wave transducer mounted in operative relation with said proximal connector end for detecting said pressure wave and providing a pressure wave signal representative thereof to said implantable medical device;

and wherein said processing means comprises a signal processing means to interpret said signal for use by said medical device.

13. The system of claim 12 wherein:

said catheter comprises a lead having an electrical conductor extending between said proximal connector end and said distal end thereof and a sense electrode coupled to said lead for making contact with a patient's heart; and said signal processing means further comprises means for bandpass filtering said pressure wave signals to detect signals associated with the contraction of the heart, if present.

14. The system of claim 13 wherein said processing means further comprises:

means for bandpass filtering said pressure wave signals to detect pressure wave signals associated with the respiratory cycle.

15. The system of claim 12 further comprising:

a reference transducer mounted in said connector assembly and isolated from said proximal connector end for detecting common mode noise signals and providing a reference signal in response thereto; and wherein said signal processing means further comprises:

means responsive to said reference signal and said pressure wave signal for removing common mode noise and detecting pressure waves associated with the contraction of the heart, if present.

16. The system of claim 12 wherein:

said catheter comprises a lead having an electrical conductor extending between said proximal connector end and said distal end thereof and a sense electrode coupled to said lead for making contact with a patient's heart; and said signal processing means further comprises means for bandpass filtering said pressure wave signals to detect signals associated with the respiratory cycle.

17. The system of claim 12 wherein said signal processing means further comprises means for filtering said pressure wave signals to detect signals associated with the activity level of the patient.

18. The system of claim 12 wherein:

said catheter comprises a lead having an electrical conductor extending between said proximal connector end and said distal end thereof and a sense electrode coupled to said lead for making contact with a patient's heart; and said signal processing means further comprises means for bandpass filtering said pressure wave signals to detect signals associated with patient's activity level.

* * * * *